(12) United States Patent
Blakley et al.

(10) Patent No.: US 7,245,961 B2
(45) Date of Patent: Jul. 17, 2007

(54) ECG ELECTRODE CHARACTERIZATION AND COMPENSATION

(75) Inventors: Daniel R. Blakley, Philomath, OR (US); Tong Zhang, San Jose, CA (US); Steven J. Simske, Fort Collins, CO (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 301 days.

(21) Appl. No.: 10/894,303

(22) Filed: Jul. 19, 2004

(65) Prior Publication Data

US 2006/0015033 A1    Jan. 19, 2006

(51) Int. Cl.
    *A61B 5/04*    (2006.01)
(52) U.S. Cl. .................................................. 600/509
(58) Field of Classification Search ................ 600/481, 600/508, 509
    See application file for complete search history.

(56) References Cited

U.S. PATENT DOCUMENTS

| | | | |
|---|---|---|---|
| 4,319,197 A | | 3/1982 | Trummer |
| 4,506,678 A | | 3/1985 | Russell et al. |
| 5,382,956 A | | 1/1995 | Baumgartner et al. |
| 5,474,574 A | | 12/1995 | Payne et al. |
| 5,522,396 A | | 6/1996 | Langer et al. |
| 5,601,089 A | | 2/1997 | Bledsoe et al. |
| 5,913,827 A | | 6/1999 | Gorman |
| 5,921,939 A | * | 7/1999 | Danielsson et al. ......... 600/509 |
| 6,186,955 B1 | | 2/2001 | Baura |
| 6,496,721 B1 | | 12/2002 | Yonce |
| 6,516,218 B1 | * | 2/2003 | Cheng et al. ............... 600/509 |
| 2002/0183797 A1 | | 12/2002 | Kaiser et al. |
| 2003/0032989 A1 | | 2/2003 | Herleikson |
| 2004/0019288 A1 | | 1/2004 | Kinast |

FOREIGN PATENT DOCUMENTS

| | | |
|---|---|---|
| EP | 0 800 787 A | 10/1997 |
| WO | WO 2004/047636 A | 6/2004 |

OTHER PUBLICATIONS

Devlin, Phillip H. et al., "Detecting Electrode Motion Noise in ECG Signals by Monitoring Electrode Impedance," Computers in Cardiology, pp. 51-56, 1984.*
McLaughlin, et al., "Novel Dry Electrode ECG Sensor System," Engineering in Medicine and Biology Society, 1994. Engineering Advances: New Opportunities for Biomedical Engineers. Proceedings of the 16th Annual International Conference of the IEEE, p. 804, 1994.*
M. J. Burke & D. T. Gleeson, A Micropower Dry-Electrode ECG Preamplifier, (IEEE Transactions on Biomedical Engineering, vol. 47, No. 2), Feb. 2000. pp. 155-162.
P. Ask et al, "ECG Electrodes", Acta Anaethesiologica Scandinavica, V.23 (2), Apr. 1979.

* cited by examiner

*Primary Examiner*—Carl Layno
*Assistant Examiner*—Eric D. Bertram

(57) ABSTRACT

Systems, methodologies, media, and other embodiments associated with electrocardiogram electrode characterization and compensation are described. One exemplary system embodiment includes a characterization logic configured to generate signals designed to facilitate characterizing an electrocardiogram electrode. The characterization logic may also be configured to analyze signals produced in response to introducing the signals into a subject. The example system may also include a compensation logic configured to determine whether an electrode is performing in a desired manner and to selectively compensate for electrode performance.

8 Claims, 7 Drawing Sheets

US 7,245,961 B2

ECG ELECTRODE CHARACTERIZATION AND COMPENSATION

BACKGROUND

Human (and other) autonomous nervous systems generate and conduct electrical signals to and from the heart muscle. These cardiac electrical signals can be monitored by an electrocardiogram (ECG) apparatus configured to receive electrical signals associated with the physical cardiac activity, which is manifested through electrical activity available generally on the surface regions of the thorax. In normal operation, an ECG can measure voltages associated with the nerve and muscles involved in cardiac activity. Thus, surface-adhering electrodes may receive electrical signals generated by cardiac activity. The electrodes may be positioned at various, specific, pre-determined locations on the body determined, for example, with reference to various electrical (e.g., resistive) models of the body or by empirical, clinical studies. In one example, the thorax can be modeled using parallel columns with two electrically conducting tissue paths. One path may include a relatively lower resistive blood path while a second path may include a relatively higher resistive tissue path. These paths may be employed to form circuits between ECG electrodes.

ECG signals and other biomedical signals may be measured as analog differential signals. Acquiring biomedical signals may involve selectively amplifying very small analog signals found in the same environment as larger common-mode signals. Both small and large signals may be present in an environment from which biomedical signals are acquired. The biomedical signals may be effectively found as additive values with respect to the measurement system. An intended measured signal may be enhanced by using differential measurement techniques since the unintended signals from the environment are normally found as common-mode signals. Thus, when subtracted using a differential amplifier, the unintended signals may be rejected or attenuated with respect to the desired signal. In practice, for ECG signals of interest, small differential analog signals may have a small amplitude (e.g., on the order of ±5 mV). Therefore, the signals typically require amplification by amplifiers capable of significant common mode rejection.

ECG electrodes employed in clinical use typically require skin preparation to achieve low impedance electrode coupling. Low impedance electrode coupling facilitates minimizing the variation of DC coupled ECG input amplifiers. However, conventional electrode impedance variations have been commonplace with DC resistance values in the 2 k$\Omega$ to 10 k$\Omega$ range. At higher frequencies, impedance may drop to a few hundred ohms, but signals of interest to an ECG are typically low frequency (e.g., less than 500 Hz).

Patient impedance measuring may be affected by impedance associated with the interface between an electrode and the patient. This impedance is often referred to as an electrode/skin impedance. The electrode/skin impedance, which may also be referred to as contact resistance, may be as high as 1 M$\Omega$. Due to the high input-impedance of amplifiers associated with receiving electrocardiac signals, small differences (e.g., 10 K$\Omega$) in skin/electrode impedance between electrodes can yield differential-mode signal amplitudes exceeding ECG signal amplitudes, which may negatively affect ECG analysis and diagnosis, by compromising accuracy of the measured values.

BRIEF DESCRIPTION OF THE DRAWINGS

The accompanying drawings, which are incorporated in and constitute a part of the specification, illustrate various example systems, methods, and so on, that illustrate various example embodiments of aspects of the invention. It will be appreciated that the illustrated element boundaries (e.g., boxes, groups of boxes, or other shapes) in the figures represent one example of the boundaries. One of ordinary skill in the art will appreciate that one element may be designed as multiple elements or that multiple elements may be designed as one element. An element shown as an internal component of another element may be implemented as an external component and vice versa. Furthermore, elements may not be drawn to scale.

DETAILED DESCRIPTION

Figure 1:
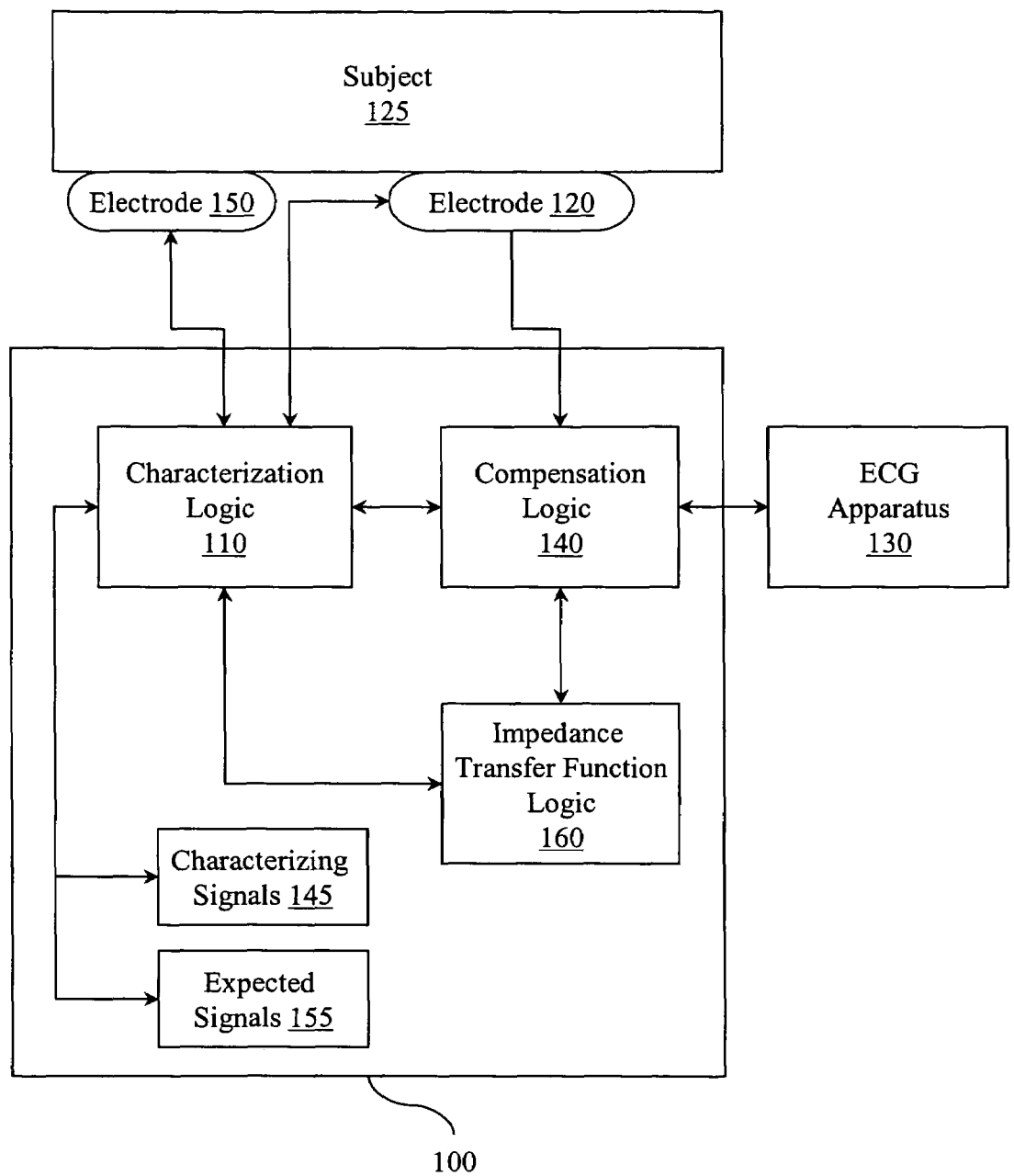
FIG. 1 illustrates an example ECG electrode characterization and compensation system.

Example systems and methods described herein concern non-intrusively characterizing electrode performance in an ECG use environment and, based on the characterization, selectively compensating for electrode performance. Thus, the example systems may facilitate making ECG signals more reliable and more accurate by correcting for signal variations due to skin/electrode impedance and/or other impedance-affecting factors (e.g., electrode location, body morphology, normally occurring skin defoliation). Clinical diagnosis involving ECG signals requires faithful preservation of the originating signal profile. The degree of faithfulness of the preservation may depend on factors associated with a skin-electrode-amplifier interface. Thus monitoring and reacting to factors associated with the skin-electrode-amplifier interface can facilitate improving clinical diagnosis involving ECG signals.

In one example, the characterization and/or compensation can be performed while a patient is attached to an ECG apparatus outside a clinical environment. The characterization and/or compensation may be performed, for example, before, during, and/or concurrently with receiving ECG signals. An example ECG apparatus may include "dry" electrodes that do not require skin surface preparation and thus, in one example, the ECG apparatus may be a wearable, ambulatory ECG unit that can be used outside a clinical setting (e.g., at home).

A dry electrode that is initially properly attached may become mis-attached over time as, for example, skin defoliates, a patient moves around, the electrode pulls away from the skin, and so on. Thus, characterizing electrode performance, initially and/or over time, facilitates longer term ECG signal acquisition by facilitating selectively compensating for variable electrode performance. In one example, as electrode performance degrades due to impedance increases, an anticipatory compensation may be computed and applied. In another example, as electrode performance degrades with increasing impedance, an ECG apparatus may be selectively deactivated if a sufficient amount of data has been acquired. This may facilitate minimizing irritation, reducing unnecessary compensations for electrode performance, and so on.

Compensations for electrode performance can include, for example, varying the gain of an ECG input amplifier associated with an electrode. ECG input amplifiers having appropriate gain and phase versus frequency characteristics facilitate preserving ECG signal profile. Having gain constant within a signal frequency range and having a sufficiently linear phase characteristic over that range facilitates preserving ECG signal profile. In one example, the American Heart Association recommends that ECG recorders have a 3 dB frequency range extending from 0.67 Hz to 150 Hz, and a substantially flat magnitude response (e.g., +/−0.5 dB) in the range 1 Hz to 30 Hz. Additionally, the American Heart Association recommends that undesired phase shifting that occurs at the lower end of the spectrum preferably not exceed that of a first-order high-pass network with a pole at 0.05 Hz.

A few general characteristics of circuits will be described as follows. Impedance (Z) is a measure of the total opposition to current flow in, for example, an alternating current (AC) circuit. It has two components: an ohmic resistance (R) and a reactance (X). The reactance is the opposition to flow of alternating current caused by inductance and capacitance in a circuit other than by resistance. Inductance is a property of an electric circuit whereby an electromotive force (EMF) is induced as the result of a changing magnetic flux. The components are related by Z=R+iX, where i=sqrt(−1). Thus, impedance can be viewed as the apparent resistance in an electric circuit to the flow of an alternating current in a manner analogous to actual resistance in a direct current (DC) circuit.

Impedance may vary between subjects and between electrodes. When there is a large impedance variation, phase and amplitude distortions may occur, which can complicate, for example, diagnosing arrhythmia, and other ECG anomalies. Impedance between electrodes can vary widely. For example, at 60 Hz, a first electrode may experience an impedance of 2400Ω while a second electrode may experience an impedance of 100,000Ω. These differential impedances result in differential voltages that may be directly interpreted as signal content that is superimposed on an intended signal and that is not reduced by the normal common-mode rejection capability of the input instrumentation amplifiers. Furthermore, impedance can change over time under a "dry" electrode because sweat may accumulate and provide an electrolytic connection with the skin. Increasing amounts of sweat may lead to a gradual decrease in impedance. While sweat is described, other factors (e.g., defoliation) may also contribute to increasing or varying impedances, over time.

In some cases where, for example, an electrode becomes unattached or otherwise unavailable, rather than attempt to compensate for an undesirable impedance transfer function, other actions may be taken. For example, systems and methods described herein may take actions like alerting a user that an electrode is unattached or that an ECG apparatus is not functioning properly, alerting a remote observer that an electrode is unattached or that an ECG apparatus is not functioning properly, powering down an ECG apparatus, and so on. Determining whether to compensate or to take (an) other action may depend, for example, on comparing impedance characteristics to pre-determined limits. These limits may be stored, for example, in a table.

Characterizing ECG electrode performance may include, for example, characterizing an amplitude response and/or a phase response in a signal transfer function as analyzed across a range of frequencies. A signal amplitude or magnitude response is associated with how the signal magnitude changes as the signal frequency changes. Similarly, a signal phase response is associated with how the signal phase changes as the signal frequency changes. Here, phase refers to a temporal or time delay, where phase is measured in radians, degrees, or absolute time as desired. Phase response is relevant to signals having a high pulse content. Delays in phase response of adjacent or varied frequencies may produce a distorted and misshaped resultant composite amplitude response due to the summation of non-linear (or non-equal time delay) pulses arriving at non-constant delays, which, when considered at a given instant, form a distorted resultant waveform when compared with the originating source. This property of linear phase is relevant to ECG signals since they naturally contain a high pulse content, especially for the peak of the QRS waveform or the "R" peak, which is often employed for analysis of measures like R-to-R values employed as a measure for arrhythmias like a-fibrillation. Determining the amplitude response and/or phase response quantitatively facilitates understanding impedance transfer functions associated with characterizing electrodes and electrode/skin interfaces. Understanding the impedance transfer function in turn helps to understand how an electrode is performing and to determine whether actions like compensating, alerting, de-activating, and the like, are desired. Further, by quantitatively measuring electrode impedance functions, appropriate compensating transfer functions may be crafted, where compensation may be made for either non-linear phase or amplitude.

As described above, ECG electrode performance may depend, for example, on a resistive element to the electrode/skin interface. Additionally, and/or alternatively, ECG electrode performance may depend, for example, on a capacitive element to the electrode/skin interface. For example, the capacitive element may vary based on electrode location, skin type, amount of subcutaneous fat, patient hydration, type of patient (e.g., human, equine, bovine, canine, feline) and so on. In one example, signal amplitude variations may depend more on electrode/skin characterization while frequency composition elements of a signal (e.g., phase, FFT) may depend more on site-specific skin capacitances. Impedance may be a combination of inductance, capacitance, and resistive elements, having characteristics of various elements, but may often be approximated by an element(s).

As indicated above, characterization and/or compensation may be performed, for example, before an ECG signal is received. This type of characterization and/or compensation may be performed as part of an initialization task. The characterization may be a partial and/or complete characterization. Additionally, and/or alternatively, the characterization and/or compensation may be performed as a background task while an ECG signal is being received. By way of illustration, subsets of characterization signals may be sent and/or received between electrocardiac signals. In one example, partial characterizations may be carried out between the T and P regions of a human cardiac waveform. Compensations may be performed based on individual partial characterizations and/or on sets of partial characterizations. For example, partial characterizations may be aggregated to facilitate performing a compensation based on a more complete characterization. The partial characterizations may be performed over several cardiac cycles, where the characterizing signals are changed between cardiac signals to facilitate acquiring a full characterization. The characterizing signals may, for example, be stepped sequentially through a range of changes, be changed according to a pre-determined pattern, be changed randomly, be changed according to an on-the-fly pattern determination, and so on. Characterization and/or compensation may also be performed as an "immediate task" during ECG signal acquisition. This type of characterization and/or compensation may include, for example, sending sets of characterization signals while ECG signal reception is suspended.

Different approaches may be taken to generate different sets and/or subsets of characterizing signals. The characterizing signals may be designed to facilitate characterizing electrode impedance transfer functions. Once characterized, electronic components, electrical components, software, and/or firmware may be employed to store an implementation of a transfer function. For example, values representing elements of polynomials that describe a numerator and a denominator of the transfer function may be stored in firmware, software, programmable gate arrays, and so on. While the example describes storing polynomial descriptive data, it is to be appreciated that other data useful for describing a transfer function may additionally and/or alternatively be stored.

The impedance transfer functions are determined, at least in part, by the contact between the electrode and the body. In one example, a set of characterizing signals may have a fixed amplitude and sweep through a range of frequencies. In another example, a set of characterizing signals may have a calibrated known amplitude that may not be fixed and sweep through a range of frequencies. In yet another example, a "chirp" or set of "chirps" may be employed. A chirp may include a set of sine-squared pulses whose frequencies are limited to those of interest. The chirp may be a signal having simultaneous or slowly varying frequency content. The set of frequencies may be generated substantially simultaneously or implicitly swept. In one example, slew rate limiting may facilitate an effective waveform that includes a characterization waveform having a suitable associated spectrum of frequencies for characterization.

Characterizing the impedance transfer functions of the electrodes facilitates determining how, if at all, the performance of an electrode is affecting ECG signals received by the electrode. If the electrode is performing within a desired range or tolerance, then received ECG signals may be passed through to downstream components (e.g., waveform analyzer, display, alarm units) substantially unchanged. Performing within a desired range or tolerance may include, for example, exhibiting a transfer function with substantially uniform amplitude and phase response. However, if the electrode is not performing within a desired range or tolerance, then compensation for non-uniform amplitude and phase response may be performed.

In one example, process based compensation may include gathering signals in response to a set of signals generated by sweeping through a frequency range of interest, characterizing amplitude and phase responses of the transfer functions associated with the electrodes, and then transforming the overall responses to facilitate storing the responses in a tabular form. The transforming may be performed, for example, by techniques including, but not limited to, Fourier transforming, wavelet transforming, Hilbert transforming, and so on. In one example, the type of transforming to be employed may be dynamically configurable based, for example, on whether amplitude, frequency, and/or phase information is being processed. The stored responses may facilitate producing corrective data employed in compensating for electrode performance. To compensate in amplitude and/or phase over the frequency range of interest, inverse corrections may be made from the corrective data derived from the transformed input data. In another example, process based compensation may include applying a set of finite impulse response (FIR) filter coefficients to an acquired input data stream. The FIR filter functions may apply an inverse complex correction factor for amplitude and/or phase with respect to frequency. While FIR filter functions are described, it is to be appreciated that other impulse response filter functions like infinite impulse response (IIR) filter functions may be employed.

The following includes definitions of selected terms employed herein. The definitions include various examples and/or forms of components that fall within the scope of a term and that may be used for implementation. The examples are not intended to be limiting. Both singular and plural forms of terms may be within the definitions.

"Computer-readable medium", as used herein, refers to a medium that participates in directly or indirectly providing signals, instructions and/or data. A computer-readable medium may take forms, including, but not limited to, non-volatile media, volatile media, and transmission media. Non-volatile media may include, for example, optical or magnetic disks, and so on. Volatile media may include, for example, optical or magnetic disks, dynamic memory and the like. Transmission media may include coaxial cables, copper wire, fiber optic cables, and the like. Transmission media can also take the form of electromagnetic radiation, like that generated during radio-wave and infra-red data communications, or take the form of one or more groups of signals. Common forms of a computer-readable medium include, but are not limited to, a floppy disk, a flexible disk, a hard disk, a magnetic tape, other magnetic media, a CD-ROM, other optical media, punch cards, paper tape, other physical media with patterns of holes, a RAM, a ROM, an EPROM, a FLASH-EPROM, or other memory chip or card, a memory stick, a carrier wave/pulse, and other media from which a computer, a processor or other electronic device can read. Signals used to propagate instructions or other software over a network, like the Internet, can be considered a "computer-readable medium."

"Logic", as used herein, includes but is not limited to hardware, firmware, software and/or combinations of each to perform a function(s) or an action(s), and/or to cause a function or action from another logic, method, and/or system. For example, based on a desired application or needs, logic may include a software controlled microprocessor, discrete logic like an application specific integrated circuit (ASIC), a programmed logic device, a memory device containing instructions, or the like. Logic may include one or more gates, combinations of gates, or other circuit components. Logic may also be fully embodied as software. Where multiple logical logics are described, it may be possible to incorporate the multiple logical logics into one physical logic. Similarly, where a single logical logic is described, it may be possible to distribute that single logical logic between multiple physical logics.

"Software", as used herein, includes but is not limited to, one or more computer or processor instructions that can be read, interpreted, compiled, and/or executed and that cause a computer, processor, or other electronic device to perform functions, actions and/or behave in a desired manner. The instructions may be embodied in various forms like routines, algorithms, modules, methods, threads, and/or programs including separate applications or code from dynamically and/or statically linked libraries. Software may also be implemented in a variety of executable and/or loadable forms including, but not limited to, a stand-alone program, a function call (local and/or remote), a servlet, an applet, instructions stored in a memory, part of an operating system or other types of executable instructions. It will be appreciated by one of ordinary skill in the art that the form of software may depend, for example, on requirements of a desired application, the environment in which it runs, and/or the desires of a designer/programmer or the like. It will also be appreciated that computer-readable and/or executable instructions can be located in one logic and/or distributed between two or more communicating, co-operating, and/or parallel processing logics and thus can be loaded and/or executed in serial, parallel, massively parallel and other manners.

Suitable software for implementing the various components of the example systems and methods described herein may be produced using programming languages and tools like Java, Pascal, C#, C++, C, CGI, Perl, SQL, APIs, SDKs, assembly, firmware, microcode, and/or other languages and tools. Software, whether an entire system or a component of a system, may be embodied as an article of manufacture and maintained or provided as part of a computer-readable medium as defined previously. Another form of the software may include signals that transmit program code of the software to a recipient over a network or other communication medium. Thus, in one example, a computer-readable medium has a form of signals that represent the software/firmware as it is downloaded from a web server to a user. In another example, the computer-readable medium has a form of the software/firmware as it is maintained on the web server. Other forms may also be used.

"User", as used herein, includes but is not limited to one or more persons, software, computers or other devices, or combinations of these.

Some portions of the detailed descriptions that follow are presented in terms of algorithms and symbolic representations of operations on data bits within a memory. These algorithmic descriptions and representations are the means used by those skilled in the art to convey the substance of their work to others. An algorithm is here, and generally, conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic and the like.

It has proven convenient at times, principally for reasons of common usage, to refer to these signals as bits, values, elements, symbols, characters, terms, numbers, or the like. It should be borne in mind, however, that these and similar terms are to be associated with the appropriate physical quantities and are merely convenient labels applied to these quantities. Unless specifically stated otherwise, it is appreciated that throughout the description, terms like processing, computing, calculating, determining, displaying, or the like, refer to actions and processes of a computer system, logic, processor, or similar electronic device that manipulates and transforms data represented as physical (electronic) quantities.

FIG. 1 illustrates an example system 100 associated with ECG electrode characterization and compensation. For explanatory purposes, the following example will be described with reference to an electrocardiogram (ECG) apparatus 130 that is configured to monitor signals that are received from a subject 125 through one or more electrodes 120. The subject 125 may be, for example, a human body, an equine body, a bovine body, a canine body, a feline body, and so on. The monitored signals may be electrocardiac signals from a heart (not shown) of the subject 125. In general, the one or more electrodes 120 are configured to detect signals from the subject 125 and provide the signals, directly and/or indirectly, to the ECG apparatus 130. The electrode 120 can be a cutaneous electrode. In one example, electrode 120 may be a dry electrode that may be attached to the subject 125 on an unprepared skin surface. Thus, system 100 may be suitable for use outside a clinical environment. While system 100 is illustrated as a separate component from the ECG apparatus 130, it is to be appreciated that the system 100 may, in some examples, be configured on and/or in the ECG apparatus 130. While a single electrode 120 is illustrated, it is to be appreciated that the characterization logic 110 may characterize a set of electrodes that detect and provide, directly and/or indirectly, signals to the ECG apparatus 130.

The system 100 may include a characterization logic 110 that is configured to characterize a signal transferring property of the electrode 120. The signal transferring property can be a performance characteristic like the impedance of the electrode 120. As previously explained, the performance characteristics of an electrode can change between different electrodes, can change due to variations in the contact between the electrode 120 and the subject 125, and can differ due to the physical properties of the subject 125 (e.g., skin properties).

In one example, the characterization logic 110 may be configured to provide a set of characterizing signals 145 to a second electrode 150 that is configured to transmit the set of characterizing signals 145 into the subject 125. While a single electrode 150 is illustrated, it is to be appreciated that a set of electrodes may be employed. Sending signals into the subject 125 via the second electrode 150 may produce resultant signals that are detected at the first electrode 120. Thus, the characterization logic 110 may be configured to receive, directly and/or indirectly, through the electrode 120, a set of property revealing signals produced in response to the set of characterizing signals 145 being transmitted into the subject 125. Thus, the characterization logic 110 may include signal generating circuit components and may include signal receiving circuit components (not shown).

The set of characterizing signals 145 transmitted by the electrode 150 may be crafted to facilitate characterizing the performance characteristic (e.g., impedance) of the electrode 120 based on the resultant signals detected by the electrode 120. For example, the resultant signals can be compared to a set of expected signals 155 having a desired range of properties. The expected signals 155 can be predetermined and associated to selected characterizing signals 145. Thus, inputting selected characterizing signals 145 into the subject 125 through electrode 150 should produce resultant signals that are detected by the electrode 120 that are within desired ranges to expected signals 155. If the resultant signals are not within desired ranges the compensation, which will be described in greater detail below, can be applied.

The set of characterizing signals 145 transmitted by the electrode 150 may include signals having amplitudes configured within a defined range of amplitudes. Similarly, the set of characterizing signals 145 may include signals having frequencies configured within a defined range of frequencies. In one example, the configurable range of amplitudes may be 1 mV to 25 mV. While 1 mV to 25 mV are described, it is to be appreciated that other ranges of amplitudes may be employed. In one example, the configurable range of frequencies may be 0.05 Hz to 128 Hz. While 0.05 Hz to 128 Hz are described, it is to be appreciated that other ranges of frequencies may be employed. In one example, a set of characterizing signals 145 with fixed amplitude but varying frequencies may be provided. In another example, a set of characterizing signals 145 with varying amplitude and fixed frequencies may be provided. In yet another example, the set of characterizing signals 145 may include a sine-squared pulse formed from a set of signals having configurable frequencies within a range of 0.05 Hz to 128 Hz. In another example, to facilitate complying with American Heart Association guidelines, the set of signals may range from 0.67 Hz to 150 Hz.

The characterization logic 110 may be configured to provide the set of characterizing signals 145 to the second electrode 150 at different times. In one example, the characterization logic 110 may provide the set of characterizing signals 145, and/or subsets thereof, before an electrocardiac signal of interest is received by the electrode 120. An electrocardiac signal of interest may be, for example, a signal that forms part of a set of signals to be analyzed for a diagnostic purpose. This may be part, for example, of an initialization or calibration process. In another example, the characterization logic 110 may provide the set of characterizing signals 145, and/or subsets thereof, substantially in parallel with receiving and processing electrocardiac signals of interest. In this example, partial characterizations may be performed in between receiving heart beat signals (e.g., between T and P portions of cycle). In another example, the characterization logic 110 may be configured to provide the set of characterizing signals 145, and/or subsets thereof, substantially in parallel with receiving and selectively ignoring electrocardiac signals of interest. In this example, the system 100 may temporarily suspend monitoring cardiac activity to "recalibrate".

In one example, the characterization logic 110 may be configured to (re)configure an impedance transfer function logic 160. The impedance transfer function logic 160 may host an impedance transfer function associated with a skin/electrode impedance associated with electrode 120. Hosting the impedance transfer function may include, for example, storing data and/or methods describing the transfer function in one of the known forms for such functions. Storing the data may be achieved, for example, in software, firmware, configurable hardware like a field programmable gate array, and so on. Thus, the impedance transfer function logic 160 may facilitate characterizing the signal transferring property of the electrode 120. Those skilled in the art of signal processing will appreciate that the impedance transfer function logic 160 may be (re)configured (e.g., (re)programmed) to implement a signal transfer function with one or more poles and zeroes, where the signal transfer function describes the impedance transfer function detected by the characterization logic 110.

The impedance transfer function is a type of function known as a transfer function. An example transfer function is a basic z-domain representation of a digital filter that expresses the filter as a ratio of two polynomials. A zero for a transfer function exists for values that force the numerator of the ratio to go to zero. Similarly, a pole for a transfer function exists for values that force the denominator of the polynomial to zero, and thus force the ratio towards infinity. It is frequently convenient to represent a digital filter, or a system of difference equations, as a set of first-order difference equations. Sets of first-order difference equations are readily characterized in software, firmware, and/or by manipulating configurable logics like FPGAs and the like.

The characterization logic 110 may be configured to analyze an amplitude response of the impedance transfer function over a range of frequencies associated with the set of characterizing signals 145, a phase response of the impedance transfer function over the range of frequencies, and so on.

The system 100 may also include a compensation logic 140 that is operably connected to the characterization logic 110. The compensation logic 140 may be configured to manipulate the electrocardiac signal received by the electrode 120. The manipulation may be based, at least in part, on the characterization of the signal transferring property performed by the characterization logic 110.

In one example, the compensation logic 140 may be configured to statically manipulate the electrocardiac signal before providing it to the electrocardiogram apparatus 130. The signal may be statically manipulated to compensate for the signal transferring property of electrode 120 not being substantially uniform in, for example, amplitude response over a range of frequencies, phase response over a range of frequencies, and so on. For example, a first characterizing signal with an amplitude of 10 mV that is transmitted into the body at 50 Hz may produce a first property revealing signal with a first amplitude and a first phase shift. The first property revealing signal may be detected at electrode 120. Similarly, a second characterizing signal with an amplitude of 10 mV that is transmitted into the body at 100 Hz may produce a second property revealing signal with a second amplitude and a second phase shift. The compensation logic 140 may be configured to facilitate manipulating electrocardiac signals in light of the varying properties revealed at the various frequencies.

Thus, compensation logic 140 may be configured to statically manipulate the electrocardiac signal by, for example, selectively providing it to a circuit component (not illustrated) that is configured to manipulate the amplitude of the electrocardiac signal. In one example, the circuit component(s) may be located in compensation logic 140, while in another example the circuit component(s) may be operably connected to compensation logic 140. The circuit component(s) may be configured to amplify and/or attenuate the signal amplitude. How and whether the amplitude is manipulated may depend, at least in part, on an amplitude response of the impedance transfer function as characterized by the characterization logic 110.

Similarly, the compensation logic 140 may be configured to statically manipulate the electrocardiac signal by selectively providing it to a circuit component (not illustrated) that is configured to manipulate the phase of the electrocardiac signal. In one example, the circuit component(s) may be located in the compensation logic 140 while in another example the circuit component(s) may be operably connected to the compensation logic 140. The circuit component may be configured to phase shift a signal. How and whether the phase is manipulated may depend, at least in part, on a phase response of the impedance transfer function as characterized by the characterization logic 110. Static compensation may include, for example, using passive and/or active circuit components to amplify and/or attenuate amplitude and/or to shift phase. The passive and/or active circuit components may be added, for example, to signal receiving elements associated with an electrode. While this paragraph describes statically manipulating the electrocardiac signal, it is to be appreciated that the electrocardiac signal(s) may also be dynamically manipulated.

Therefore, the compensation logic 140 may be configured to dynamically manipulate the electrocardiac signal before providing it to the electrocardiogram apparatus 130. Dynamic compensation may include, for example, using passive and/or dynamic circuit components to amplify and/or attenuate amplitude and/or to shift phase. Furthermore, dynamic compensation may also include, for example, using process based (e.g., software, firmware) compensation. The signal may be manipulated to compensate, for example, for the signal transferring property of electrode 120 not being within a desired tolerance (e.g., not being substantially uniform) on an attribute. For example, the electrode 120 may not exhibit desirable performance in amplitude response over a range of frequencies, phase response over a range of frequencies, and so on.

Thus, the compensation logic 140 may be configured to dynamically manipulate (e.g., amplify, attenuate, phase shift, high pass filter, low pass filter, band pass filter) the electrocardiac signal. The manipulation may be performed, for example, by selectively providing the electrocardiac signal to circuit components (not illustrated) configured to manipulate the amplitude of the electrocardiac signal.

In another example, the compensation logic 140 may be configured to dynamically manipulate the electrocardiac signal by selectively providing the electrocardiac signal to a logic configured to selectively reconfigure the impedance transfer logic 160. For example, the characterization logic 110 may be configured to reconfigure the impedance transfer logic 160 by manipulating (e.g., adding, deleting, changing) values stored in the impedance transfer logic 160, where the values describe the impedance transfer function. Reconfiguring the impedance transfer logic 160 may include, for example, logically adding a pole and/or a zero to the impedance transfer function hosted by the impedance transfer logic 160. Logically adding a pole or zero may be accomplished programmatically in software or firmware. Logically adding a pole or zero may also be accomplished by dynamically reconfiguring a configurable logic like a FPGA, and the like. Whether a pole or zero is logically added to the impedance transfer function may be determined, for example, by an amplitude response of the impedance transfer function over a range of frequencies as characterized by the characterization logic 110. Similarly, whether a pole or zero is added to the impedance transfer function may be determined by a phase response of the impedance transfer function over a range of frequencies as characterized by the characterization logic 110. Depending on the characteristics of the impedance transfer function correction required, either analog and/or digital pole and/or zero corrections may be made.

In another example, the compensation logic 140 may be configured to dynamically manipulate the electrocardiac signal by manipulating the phase and/or amplitude of the electrocardiac signal where the degree to which the phase and/or amplitude will be manipulated may be determined, for example, by corrective data. The corrective data may be derived from inverse transforms (e.g., Fourier, wavelet, Hilbert) applied to transformed data associated with characterizing the signal transferring property of the electrode(s) 120. The type of inverse transformation performed may depend, for example, on whether amplitude, frequency, and/or phase data is being processed.

In another example, the compensation logic 140 may be configured to statically manipulate the electrocardiac signal received through the electrode(s) 120 by applying a set of impulse response filter coefficients to the electrocardiac signal. Impulse response filter coefficients may include, for example, finite impulse response filter coefficients and infinite impulse response filter coefficients. Applying the set of impulse response filter coefficients may facilitate producing an inverse complex correction factor for the amplitude with respect to frequency and/or for the phase with respect to frequency.

Figure 2:
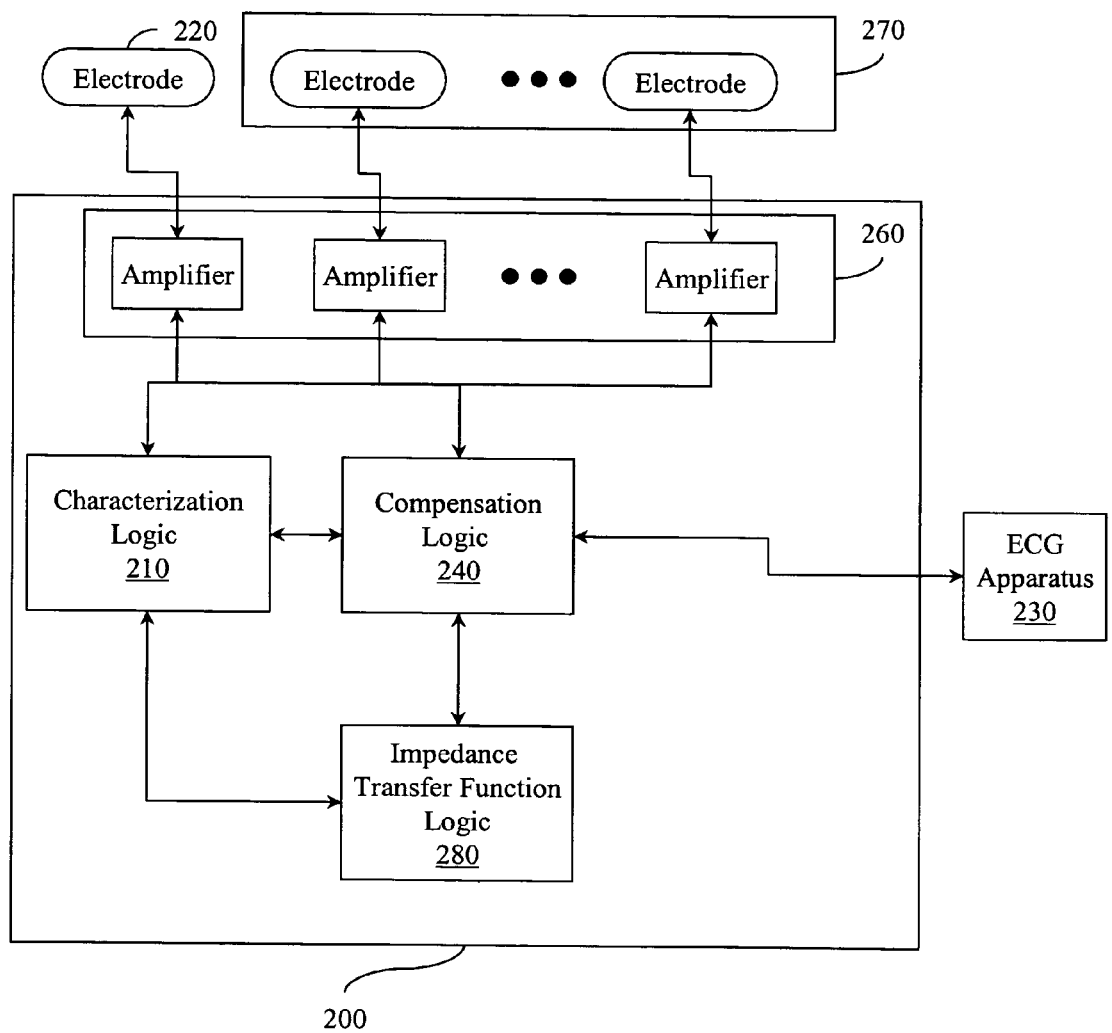
FIG. 2 illustrates another example ECG electrode characterization and compensation system.

FIG. 2 illustrates an example system 200 that is configured to facilitate ECG electrode characterization and compensation. The system 200 may include, similar to system 100 (FIG. 1), a characterization logic 210, and a compensation logic 240. The system 200 may be configured to provide an electrocardiac signal detected by a first electrode(s) 220 to an ECG apparatus 230. Like system 100, system 200 may be configured to be located in, on, and/or separate from the ECG apparatus 230.

Additionally, system 200 may include a set of AC-coupled amplifiers 260. AC-coupling refers to a form of electrical recording that retains changing events and not underlying steady (e.g., DC) currents. An AC-coupled differential amplifier facilitates selectively amplifying a small time varying analog biomedical signal (e.g., ECG signal) while rejecting other signals like common mode, DC, and low frequency signals. AC-coupled amplifiers with "true" AC-coupled inputs have input capacitors that may act as high pass filters and block DC and low frequency signals. Electrodes that are applied to unprepared skin and whose input amplifiers are AC-coupled may experience higher impedance across the skin surface and thus lower impedance variations across different low frequencies that are associated with the AC coupling of the associated amplifiers.

Members of the set of amplifiers 260 may be operably connected to electrode(s) 220 and a set of similar electrodes 270 associated with the electrocardiogram apparatus 230. The set of electrodes 270, like electrode(s) 220, may be configured to receive electrocardiac signals from a heart to be monitored by the electrocardiogram apparatus 230. Thus, the set of AC-coupled amplifiers 260 may be configured to receive and manipulate (e.g., amplify, attenuate) the electrocardiac signals. While a set of AC-coupled amplifiers 260 is illustrated, it is to be appreciated that other amplifier configurations may be employed. For example, system 200 may include a set (not illustrated) of DC-coupled amplifiers. The DC-coupled amplifiers may be operably connected to the electrode 220 and/or electrodes 270. The DC-coupled amplifiers may therefore be configured to receive and manipulate electrocardiac signals to be provided to the electrocardiac system 230. However, the DC-coupled amplifiers may also be operably connected to a simulation logic (not illustrated) that is configured to simulate AC-coupling between the set of DC-coupled amplifiers. Simulating AC-coupling may be achieved, for example, by having the simulation logic apply a high pass filter operation to the electrocardiac signal. The high pass filter operation may be performed, for example, during the ECG recording and/or after the ECG recording as part of a post-filtering phase.

Figure 3:
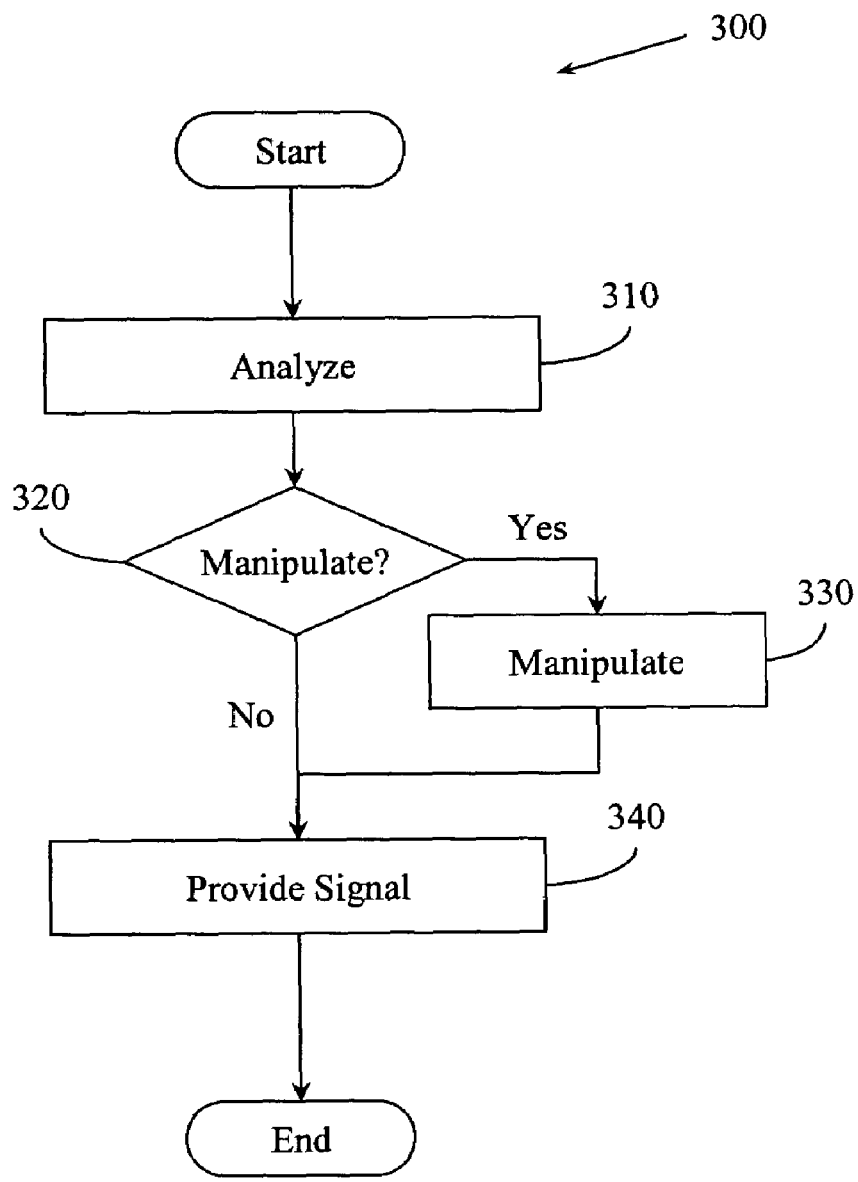
FIG. 3 illustrates an example method associated with ECG electrode characterization and compensation.
Figure 4:
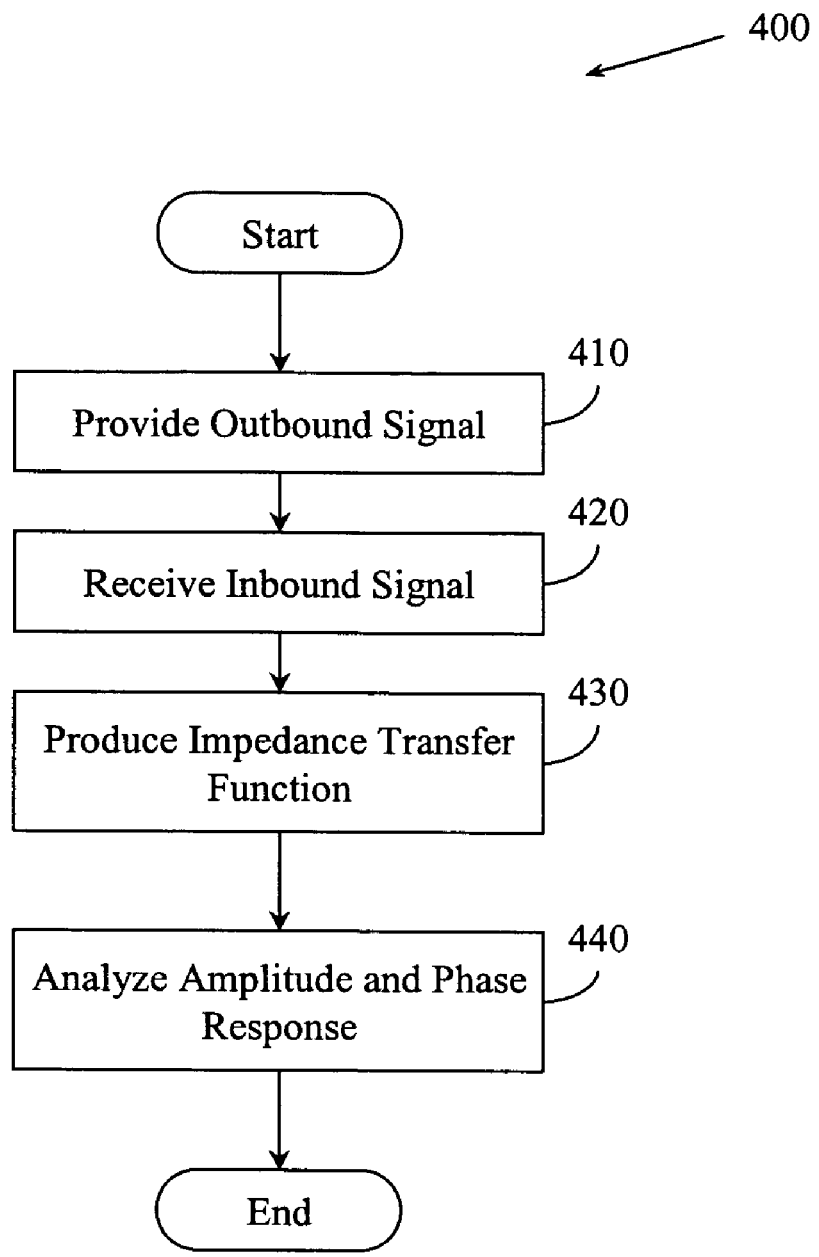
FIG. 4 illustrates another example method associated with ECG electrode characterization and compensation.
Figure 5:
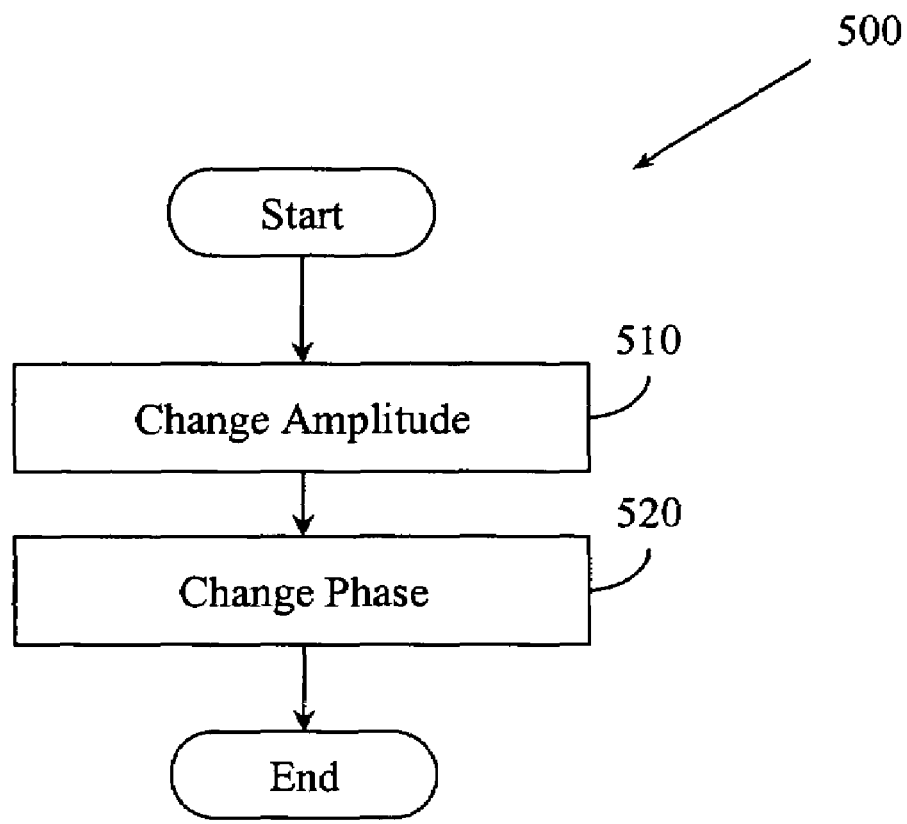
FIG. 5 illustrates another example method associated with ECG electrode characterization and compensation.

Example methods may be better appreciated with reference to the flow diagrams of FIGS. 3 through 5. While for purposes of simplicity of explanation, the illustrated methodologies are shown and described as a series of blocks, it is to be appreciated that the methodologies are not limited by the order of the blocks as some blocks can occur in different orders and/or concurrently with other blocks from that shown and described. Moreover, less than all the illustrated blocks may be required to implement an example methodology. Furthermore, additional and/or alternative methodologies can employ additional, not illustrated blocks.

In the flow diagrams, blocks denote "processing blocks" that may be implemented with logic. The processing blocks may represent a method step and/or an apparatus element for performing the method step. A flow diagram does not depict syntax for any particular programming language, methodology, or style (e.g., procedural, object-oriented). Rather, a flow diagram illustrates functional information one skilled in the art may employ to develop logic to perform the illustrated processing. It will be appreciated that in some examples, program elements like temporary variables, routine loops, and so on, are not shown. It will be further appreciated that electronic and software applications may involve dynamic and flexible processes so that the illustrated blocks can be performed in other sequences that are different from those shown and/or that blocks may be combined or separated into multiple components. It will be appreciated that the processes may be implemented using various programming approaches like state-machines, machine language, procedural, object oriented and/or artificial intelligence techniques.

FIG. 3 illustrates an example method 300 associated with ECG electrode characterization and compensation. Method 300 may include, at 310, analyzing a performance characteristic of an electrode associated with an electrocardiogram apparatus. In one example, the electrode may be configured to receive an electrocardiac signal from a heart to be monitored by the electrocardiogram apparatus. Analyzing the performance characteristic may include several actions like analyzing phase, frequency, and/or amplitude response. One example set of actions is illustrated in FIG. 4.

Method 300 may also include, at 320, determining whether to manipulate the electrocardiac signal received at the electrode. The determination at 320 may be based, for example, on the analysis 310 of the performance characteristic of the electrode. For example, if the electrode is performing within a desired tolerance, then the electrocardiac signal may not be manipulated by compensation. However, if the electrode is not performing within a desired tolerance, then the electrocardiac signal may be manipulated to compensate for the out of tolerance performance. In one example, the determination at 320 may be a multi-way decision. For example, in addition to determining whether to manipulate an electrocardiac signal, a determination may be made concerning whether to take other actions like alerting a user that an electrode(s) may be unattached, powering down the ECG system, and so on.

If the determination at 320 is yes, that the signal should be manipulated, then at 330 the electrocardiac signal may be manipulated to compensate for the out of tolerance performance. Manipulating the signal may include several actions like amplifying, attenuating, phase shifting, filtering, and so on. One example set of actions is illustrated in FIG. 5. Method 300 may also include, at 340, providing electrocardiac signals, either original or manipulated, to the electrocardiogram apparatus.

While FIG. 3 illustrates various actions occurring in serial, it is to be appreciated that various actions illustrated in FIG. 3 could occur substantially in parallel. By way of illustration, a first process could analyze electrode performance, a second process could manipulate an electrocardiac signal and a third process could provide the manipulated electrocardiac signal to an ECG apparatus. While three processes are described, it is to be appreciated that a greater and/or lesser number of processes could be employed and that lightweight processes, regular processes, threads, and other approaches could be employed. It is to be appreciated that other example methods may, in some cases, also include actions that occur substantially in parallel.

As described above, analyzing the performance characteristic of the electrode at 310 (FIG. 3) may include one or more actions. Thus, FIG. 4 illustrates a method 400 where analyzing the performance characteristic of the electrode may include, at 410, providing (e.g., producing, transmitting), directly and/or indirectly, a set of outbound signals to an electrode tasked with transmitting signals into a body. To facilitate characterizing an amplitude and/or phase response in a signal transfer function associated with an electrode, the set of outbound signals may vary in amplitude and/or frequency. Thus, in one example, the set of outbound signals facilitates analyzing an electrode/skin impedance associated with the electrode as applied to the body. Signals resulting from providing 410 the outbound signals may be received at 420.

In one example, the set of the outbound signals and/or subsets thereof may be provided at 410, and the inbound signals received at 420 at times including, but not limited to, before an electrocardiac signal of interest is received by the electrode, substantially in parallel with receiving and processing an electrocardiac signal of interest, and substantially in parallel with receiving and selectively ignoring an electrocardiac signal.

Analyzing the electrode/skin impedance may include, at 430, producing an impedance transfer function that describes a signal processing characteristic (e.g., impedance) of the electrode. Producing the impedance transfer function may include, in one example, determining an approximation (e.g., mathematical) of the transfer function. In that example, adding a pole or zero to the transfer function may include adding and/or manipulating terms in the approximation. For example, data representing additional terms for a numerator polynomial and/or a denominator polynomial may be manipulated (e.g., added, deleted, changed). Producing the impedance transfer function may include, in another example, configuring a configurable logic (e.g., FPGA, DSP) to simulate the transfer function. In that example, adding a pole or zero to the transfer function may include reconfiguring the configurable logic to simulate addition of the new pole or zero.

Analyzing the electrode/skin impedance may also include, at 440, analyzing the phase response and/or amplitude response of the impedance transfer function over a range of frequencies. Characterizing the performance of an electrode facilitates, for example, being able to compensate for variations in performance of an electrode(s).

As described above, manipulating the signal to, for example, compensate for electrode performance variations may include several actions. FIG. 5 illustrates a portion of a method 500 associated with manipulating an electrocardiac signal. Method 500 may include, at 510, manipulating an electrocardiac signal by selectively amplifying and/or attenuating the signal. It is to be appreciated that the amplification and/or attenuation may be performed statically and/or dynamically. Method 500 may also include, at 520, selectively phase shifting the electrocardiac signal. Again, the phase shifting may be performed statically and/or dynamically. The degree to which the signal is amplified, attenuated, and/or phase shifted may depend, for example, on a relationship between an observed performance of the electrode and a desired performance for the electrode. While amplifying, attenuating, and phase shifting are described, it is to be appreciated that other actions like filtering may be taken.

In one example, the amount by which the amplitude and/or phase is manipulated may be determined, at least in part, by a corrective data. The corrective data may be, for example, inverse Fourier corrective data, inverse wavelet transform data, inverse Hilbert transform data, and so on. The corrective data may be derived, for example, from a transformed input data that is acquired while analyzing the performance characteristic of the electrode. Which type of corrective data is employed may depend, for example, on whether amplitude, frequency, and/or phase data is being processed. In one example, amplitude and/or phase may be manipulated by applying a set of impulse response filter coefficients to the electrocardiac signal to effect an inverse complex correction. The impulse response filter coefficients may include, for example, finite impulse response filters, infinite impulse response filter coefficients, and so on. The inverse complex correction may be applied, for example, to the amplitude with respect to frequency, the phase with respect to frequency, and so on.

The ability to detect variations in electrode performance and then, in real-time in the use environment to compensate for the detected variations facilitates, for example, employing electrocardiogram equipment outside a clinical setting where dry electrodes may be applied by unskilled people (e.g., a patient) to unprepared skin.

In one example, methodologies are implemented as processor executable instructions and/or operations provided on a computer-readable medium. Thus, in one example, a computer-readable medium may store processor executable instructions operable to perform a method that includes analyzing a performance characteristic of an electrode associated with an electrocardiogram apparatus. The electrode may be configured to receive an electrocardiac signal from a heart to be monitored by the electrocardiogram apparatus. Analyzing the performance characteristic may include, for example, providing a set of outbound signals that vary in amplitude, frequency, and so on. The outbound signals may be provided to a second electrode that is configured to transmit the outbound signals into a body. The outbound signals may facilitate analyzing an electrode/skin impedance associated with the electrode as applied to the body. Analyzing the electrode/skin impedance may include, for example, producing an impedance transfer function that describes a signal processing operation of the electrode. Analyzing the electrode/skin impedance may also include, for example, analyzing the phase response and magnitude response of the impedance transfer function over a range of frequencies. Furthermore, analyzing the electrode/skin impedance may include receiving a set of inbound signals produced by the set of outbound signals transiting the body. The method may also include selectively manipulating the electrocardiac signal received at the electrode based on the performance characteristic of the electrode as analyzed by the method. The method may also include providing the electrocardiac signal to the electrocardiogram apparatus. While the above method is described being provided on a computer-readable medium, it is to be appreciated that other example methods described herein can also be provided on a computer-readable medium.

Figure 6:
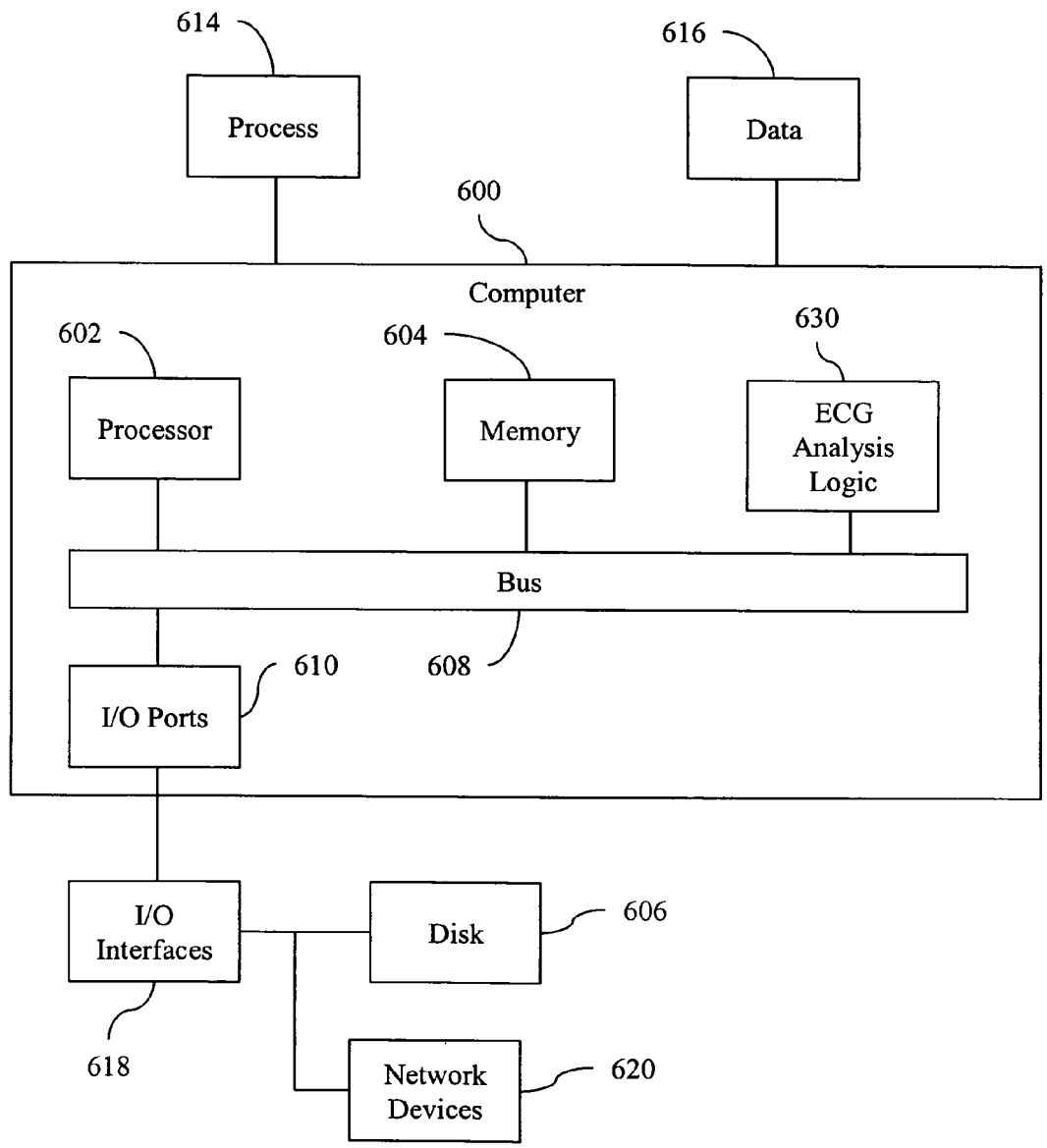
FIG. 6 illustrates an example computing environment in which example systems and methods illustrated herein can operate.

FIG. 6 illustrates a computer 600 that includes a processor 602, a memory 604, and input/output ports 610 operably connected by a bus 608. In one example, the computer 600 may include an ECG analysis logic 630 that is configured to facilitate characterizing an ECG electrode and compensating for performance variations within and/or between various ECG electrodes. Thus, the ECG analysis logic 630, whether implemented in computer 600 as hardware, firmware, software, and/or a combination thereof may provide means for characterizing an impedance characteristic of an electrode associated with an electrocardiogram apparatus. The electrode may be, for example, a dry electrode that is applied to an unprepared surface on a human body. The electrode may be applied outside a clinical setting by, for example, a patient. The electrode may be configured to detect an electrocardiac signal associated with a heart to be monitored by the electrocardiogram apparatus. The ECG analysis logic 630 may also provide, for example, means for selectively manipulating an electrocardiac signal received at the electrode. How the electrocardiac signal is manipulated may be based, for example, on the characterizing of the impedance characteristic of the electrode.

The processor 602 can be a variety of various processors including digital signal processors, dual microprocessor or dual digital signal processor, and other multi-processor architectures. The memory 604 can include volatile memory and/or non-volatile memory. The non-volatile memory can include, but is not limited to, ROM, PROM, EPROM, EEPROM, FLASH, FROM and the like. Volatile memory can include, for example, RAM, synchronous RAM (SRAM), dynamic RAM (DRAM), synchronous DRAM (SDRAM), double data rate SDRAM (DDR SDRAM), and direct RAM bus RAM (DRRAM).

A disk 606 may be operably connected to the computer 600 via, for example, an input/output interface (e.g., card, device) 618 and an input/output port 610. The disk 606 can include, but is not limited to, devices like a magnetic disk drive, a solid state disk drive, a floppy disk drive, a tape drive, a Zip drive, a flash memory card, and/or a memory stick. Furthermore, the disk 606 can include optical drives like a CD-ROM, a CD recordable drive (CD-R drive), a CD rewriteable drive (CD-RW drive), and/or a digital video ROM drive (DVD ROM). The memory 604 can store processes 614 and/or data 616, for example. The disk 606 and/or memory 604 can store an operating system that controls and allocates resources of the computer 600.

The bus 608 can be a single internal bus interconnect architecture and/or other bus or mesh architectures. While a single bus is illustrated, it is to be appreciated that computer 600 may communicate with various devices, logics, and peripherals using other busses that are not illustrated (e.g., PCIE, SATA, Infiniband, 1394, USB, Ethernet). The bus 608 can be of a variety of types including, but not limited to, a memory bus or memory controller, a peripheral bus or external bus, a crossbar switch, and/or a local bus. The local bus can be of varieties including, but not limited to, an industrial standard architecture (ISA) bus, a microchannel architecture (MSA) bus, an extended ISA (EISA) bus, a peripheral component interconnect (PCI) bus, a universal serial (USB) bus, and a small computer systems interface (SCSI) bus.

The computer 600 may interact with input/output devices via I/O interfaces 618 and input/output ports 610. Input/output devices can include, but are not limited to, a keyboard, a microphone, a pointing and selection device, cameras, video cards, displays, disk 606, network devices 620, and the like. The input/output ports 610 can include but are not limited to, serial ports, parallel ports, and USB ports.

The computer 600 can operate in a network environment and thus may be connected to network devices 620 via the I/O interfaces 618, and/or the I/O ports 610. Through the network devices 620, the computer 600 may interact with a network. Through the network, the computer 600 may be logically connected to remote computers. The networks with which the computer 600 may interact include, but are not limited to, a local area network (LAN), a wide area network (WAN), and other networks. The network devices 620 can connect to LAN technologies including, but not limited to, fiber distributed data interface (FDDI), copper distributed data interface (CDDI), Ethernet (IEEE 802.3), token ring (IEEE 802.5), wireless computer communication (IEEE 802.11), Bluetooth (IEEE 802.15.1), Zigbee (IEEE 802.15.4) and the like. Similarly, the network devices 620 can connect to WAN technologies including, but not limited to, point to point links, circuit switching networks like integrated services digital networks (ISDN), packet switching networks, and digital subscriber lines (DSL). While individual network types are described, it is to be appreciated that communications via, over, and/or through a network may include combinations and mixtures of communications.

Computer 600 may be part, for example, of an ECG apparatus. Thus, in one example, an electrocardiogram apparatus configured to monitor an electrocardiac signal from a heart may be configured with an apparatus (e.g., computer 600, logic 630) that facilitates characterizing and/or compensating for electrode performance variations. In another example, an ECG apparatus may be configured with a skin/electrode impedance transfer function logic that is configured to characterize an impedance characteristic of an electrode that is configured to detect and provide the electrocardiac signal to the electrocardiogram apparatus. In one example, the skin/electrode impedance transfer logic may also being configured to selectively manipulate the electrocardiac signal before providing the electrocardiac signal to the electrocardiogram apparatus. The manipulation may be based, for example, on the characterizing of the impedance characteristic of the electrode. In another example, the skin/electrode impedance transfer logic may also be configured to report when an electrode may be unattached.

Figure 7:
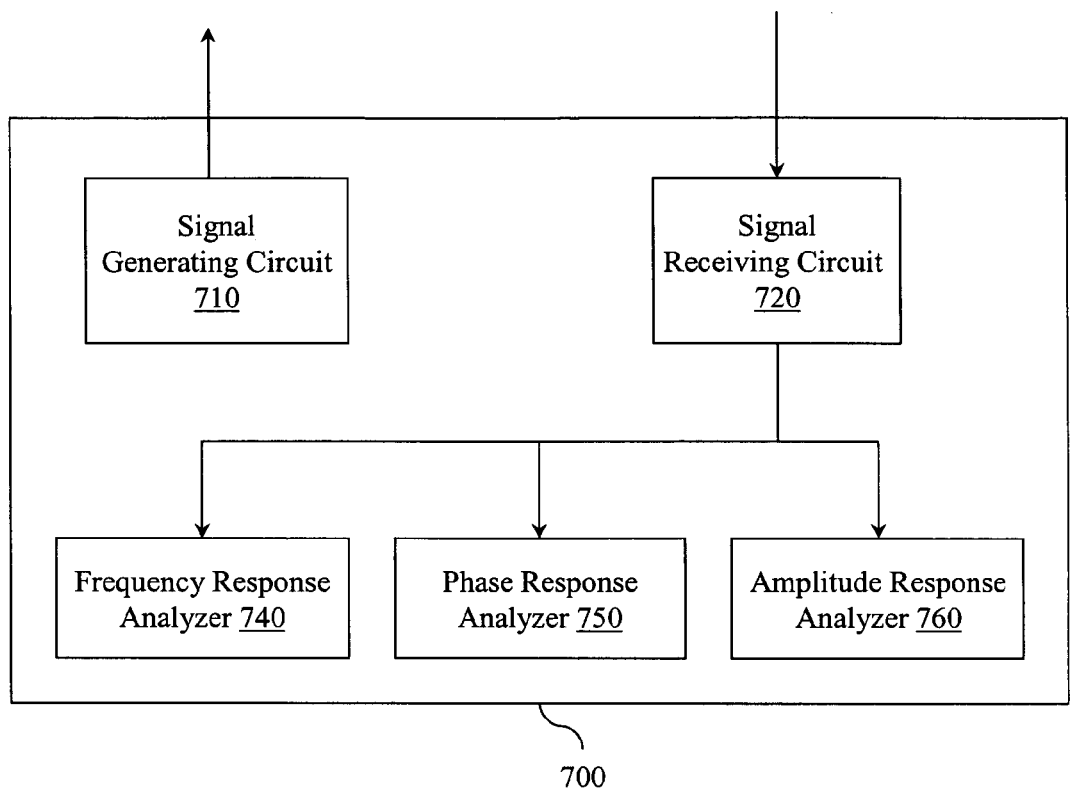
FIG. 7 illustrates an example characterization logic.

FIG. 7 illustrates an example characterization logic 700. As described above, the characterization logic 700 may be configured to provide signals to an electrode, where the signals will be passed into a body to facilitate characterizing an electrode performance by analyzing impedance transfer characteristics. Thus, the characterization logic 700 may include a signal generating circuit 710 that is configured to provide signals with, for example, varying frequencies, amplitudes, phases, and so on, to facilitate this characterization. While the signal generating circuit 710 is illustrated inside characterization logic 700, it is to be appreciated that the signal generating circuit 710 may, in other examples, be operably connected to and controlled by the characterization logic 700.

The characterization logic 700 may also be configured to receive signals from an electrode, where the signals have been passed through a body and received at the electrode. The signals received are signals produced in response to the signals from the signal generating circuit 710 being passed into the body. Therefore the characterization logic 700 may also include a signal receiving circuit 720 configured to receive the signals from the electrode(s). Since the signals are passed into the body and then received to facilitate analyzing electrode performance through characterizing impedance transfer characteristics, the signal receiving circuit 720 may be operably connected to several analyzers. These analyzers may be implemented, for example, in software, firmware, hardware, logic, and so on.

A frequency response analyzer 740 may be operably connected to the signal receiving circuit 720 to facilitate determining a frequency response associated with the received signal(s). Similarly, a phase response analyzer 750 and an amplitude response analyzer 760 may be operably connected to the signal receiving circuit 720 to facilitate determining phase and amplitude responses. While the signal receiving circuit 720 and the analyzers 740, 750, and 760 are illustrated inside the characterization logic 700, it is to be appreciated that in some examples one or more of these elements may be operably connected to the characterization logic 700 and not physically reside inside the characterization logic 700.

While example systems, methods, and so on, have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on, described herein. Additional advantages and modifications will readily appear to those skilled in the art. Therefore, the invention is not limited to the specific details, the representative apparatus, and illustrative examples shown and described. Thus, this application is intended to embrace alterations, modifications, and variations that fall within the scope of the appended claims. Furthermore, the preceding description is not meant to limit the scope of the invention. Rather, the scope of the invention is to be determined by the appended claims and their equivalents.

To the extent that the term "includes" or "including" is employed in the detailed description or the claims, it is intended to be inclusive in a manner similar to the term "comprising" as that term is interpreted when employed as a transitional word in a claim. Furthermore, to the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

What is claimed is:

1. A system, comprising:
a data processing device having logic elements provided therein as one of, or a combination of, circuit components, or as computer readable code stored on a processor readable media, said logic elements comprising:
a characterization logic configured to characterize a signal transferring property of a first electrode associated with an electrocardiogram (ECG) apparatus, the first electrode being configured to receive electrocardiac signals from a subject to be monitored by the electrocardiogram apparatus; and
a compensation logic operably connected to the characterization logic, the compensation logic being configured to manipulate electrocardiac signals received by the first electrode based, at least in part, on the characterization of the signal transferring property;
the characterization logic being configured to provide a set of characterizing signals to a second electrode configured to transmit the set of characterizing signals into the subject, the characterization logic being configured to receive through the first electrode a set of property revealing signals produced in response to the set of characterizing signals being transmitted into the subject;
the characterization logic being configured to configure an impedance transfer function logic with an impedance transfer function that characterizes a skin/electrode impedance associated with the first electrode;

the impedance transfer function logic being configured with data values representing a mathematical approximation of the impedance transfer function that characterizes the skin/electrode impedance associated with the first electrode;

and the compensation logic being configured to dynamically manipulate the electrocardiac signal by selectively providing the electrocardiac signal to a logic configured to selectively reconfigure the impedance transfer logic to add one or more of, a pole, and a zero to the impedance transfer function by manipulating a data value representing an additional term to the mathematical approximation of the impedance transfer function based, at least in part, on one or more of, an amplitude response of the impedance transfer function over a range of frequencies, and a frequency response of the impedance transfer function over a range of frequencies.

2. A system, comprising:

a data processing device having logic elements provided therein as one of, or a combination of, circuit components, or as computer readable code stored on a processor readable media, said logic elements comprising:

a characterization logic configured to characterize a signal transferring property of a first electrode associated with an electrocardiogram (ECG) apparatus, the first electrode being configured to receive electrocardiac signals from a subject to be monitored by the electrocardiogram apparatus; and a compensation logic operably connected to the characterization logic, the compensation logic being configured to manipulate electrocardiac signals received by the first electrode based, at least in part, on the characterization of the signal transferring property;

the characterization logic being configured to provide a set of characterizing signals to a second electrode configured to transmit the set of characterizing signals into the subject, the characterization logic being configured to receive through the first electrode a set of property revealing signals produced in response to the set of characterizing signals being transmitted into the subject;

the characterization logic being configured to configure an impedance transfer function logic with an impedance transfer function that characterizes a skin/electrode impedance associated with the first electrode;

the impedance transfer function logic comprising a field programmable gate array (FPGA) configured to simulate the impedance transfer function;

and the compensation logic being configured to dynamically manipulate the electrocardiac signal by selectively providing the electrocardiac signal to a logic configured to selectively reconfigure the impedance transfer logic to add one or more of, a pole, and a zero to the impedance transfer function by reconfiguring the field programmable gate array based, at least in part, on one or more of, an amplitude response of the impedance transfer function over a range of frequencies, and a frequency response of the impedance transfer function over a range of frequencies.

3. A system comprising:

an electrocardiogram (ECG) apparatus having a plurality of associated electrodes; and a data processing device having logic elements provided therein as one of, or a combination of, circuit components or as computer readable code stored on a processor readable media, said logic elements comprising:

a characterization logic configured to characterize signal transferring property of a first electrode associated with the electrocardiogram apparatus, the first electrode being configured to receive electrocardiac signals from a subject to be monitored by the electrocardiogram apparatus;

a compensation logic operably connected to the characterization logic, the compensation logic being configured to manipulate electrocardiac signals received by the first electrode based, at least in part, on the characterization of the signal transferring property;

the characterization logic being configured to provide a set of characterizing signals to a second electrode configured to transmit the set of characterizing signals into the subject, the characterization logic being configured to receive through the first electrode a set of property revealing signals produced in response to the set of characterizing signals being transmitted into the subject;

the characterization logic being configured to configure an impedance transfer function logic with an impedance transfer function that characterizes a skin/electrode impedance associated with the first electrode; and a set of DC-coupled amplifiers operably connected to the first electrode and one or more additional electrodes associated with the electrocardiogram apparatus, the one or more additional electrodes being configured to receive electrocardiac signals from a heart to be monitored by the electrocardiogram apparatus, the set of DC-coupled amplifiers being configured to receive and manipulate the electrocardiac signals, the set of DC-coupled amplifiers being operably connected to a simulation logic configured to simulate AC-coupling between the set of DC-coupled amplifiers by applying a high pass filter operation to the electrocardiac signal.

4. A system, comprising:

a data processing device having logic elements provided therein as one of, or a combination of, circuit components, or as computer readable code stored on a processor readable media, said logic elements comprising:

a characterization logic configured to characterize a signal transferring property of a first electrode associated with an electrocardiogram (ECG) apparatus, the first electrode being configured to receive electrocardiac signals from a subject to be monitored by the electrocardiogram apparatus; and a compensation logic operably connected to the characterization logic, the compensation logic being configured to manipulate electrocardiac signals received by the first electrode based, at least in part, on the characterization of the signal transferring property;

the characterization logic being configured to provide a set of characterizing signals to a second electrode configured to transmit the set of characterizing signals into the subject, the characterization logic being configured to receive through the first electrode a set of property revealing signals produced in response to the set of characterizing signals being transmitted into the subject;

the characterization logic being configured to configure an impedance transfer function logic with an impedance transfer function that characterizes a skin/electrode impedance associated with the first electrode;

and the compensation logic being configured to dynamically manipulate the electrocardiac signal by selectively providing the electrocardiac signal to a logic configured to selectively reconfigure the impedance transfer logic to add one or more of, a pole, and a zero to the impedance transfer function based, at least in part, on one or more of, an amplitude response of the impedance transfer function over a range of frequencies, and a frequency response at the impedance transfer function over a range of frequencies.

5. A system, comprising:

a data processing device having logic elements provided therein as one of, or a combination of, circuit components, or as computer readable code stored on a processor readable media, said logic elements comprising:

a characterization logic configured to characterize a signal transferring property of a first electrode associated with an electrocardiogram (ECG) apparatus, the first electrode being configured to receive electrocardiac signals from a subject to be monitored by the electrocardiogram apparatus; and a compensation logic operably connected to the characterization logic, the compensation logic being configured to manipulate electrocardiac signals received by the first electrode based, at least in part, on the characterization of the signal transferring property;

the characterization logic being configured to provide a set of characterizing signals to a second electrode configured to transmit the set of characterizing signals into the subject, the characterization logic being configured to receive through the first electrode a set of property revealing signals produced in response to the set of characterizing signals being transmitted into the subject;

the characterization logic being configured to configure an impedance transfer function logic with an impedance transfer function that characterizes a skin/electrode impedance associated with the first electrode;

and the compensation logic being configured to dynamically manipulate the electrocardiac signal by manipulating one or more of, the phase of the electrocardiac signal, and the amplitude of the electrocardiac signal by an amount determined, at least in part, by an inverse corrective data derived from a transformed input data acquired during the characterizing of the signal transferring property.

6. The system of claim 5, the transformed input data comprising one or more of, a Fourier transformed input data, a wavelet transformed input data, or a Hilbert transformed input data.

7. A system, comprising:

a data processing device having logic elements provided therein as one of, or a combination of, circuit components, or as computer readable code stored on a processor readable media, said logic elements comprising:

a characterization logic configured to characterize a signal transferring property of a first electrode associated with an electrocardiogram (ECG) apparatus, the first electrode being configured to receive electrocardiac signals from a subject to be monitored by the electrocardiogram apparatus; and a compensation logic operably connected to the characterization logic, the compensation logic being configured to manipulate electrocardiac signals received by the first electrode based, at least in part, on the characterization of the signal transferring property;

the characterization logic being configured to provide a set of characterizing signals to a second electrode configured to transmit the set of characterizing signals into the subject, the characterization logic being configured to receive through the first electrode a set of property revealing signals produced in response to the set of characterizing signals being transmitted into the subject;

the characterization logic being configured to configure an impedance transfer function logic with an impedance transfer function that characterizes a skin/electrode impedance associated with the first electrode;

and the compensation logic being configured to dynamically manipulate the electrocardiac signal by applying a set of impulse response filter coefficients to the electrocardiac signal to produce an inverse complex correction factor for one or more of, amplitude with respect to frequency, and phase with respect to frequency.

8. The system of claim 7, the impulse filter coefficients comprising one or more of, finite impulse response filter coefficients, or infinite impulse response filter coefficients.

* * * * *

UNITED STATES PATENT AND TRADEMARK OFFICE
CERTIFICATE OF CORRECTION

| | |
|---|---|
| PATENT NO. | : 7,245,961 B2 |
| APPLICATION NO. | : 10/894303 |
| DATED | : July 17, 2007 |
| INVENTOR(S) | : Daniel R. Blakley et al. |

It is certified that error appears in the above-identified patent and that said Letters Patent is hereby corrected as shown below:

In column 19, line 63, in Claim 3, after "system" insert -- , --.

In column 20, line 3, in Claim 3, after "characterize" insert -- a --.

In column 21, line 7, in Claim 4, delete "at" and insert -- of --, therefor.

Signed and Sealed this

Twenty-third Day of September, 2008

JON W. DUDAS
*Director of the United States Patent and Trademark Office*